(12) United States Patent
Reischman

(10) Patent No.: US 7,741,122 B2
(45) Date of Patent: Jun. 22, 2010

(54) DETERMINATION OF TOTAL BASE NUMBER IN MARINE ENGINE LUBRICANTS BY ELEMENTS

(75) Inventor: P. Thomas Reischman, Lambertville, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 27 days.

(21) Appl. No.: 11/701,631

(22) Filed: Feb. 2, 2007

(65) Prior Publication Data

US 2007/0196925 A1 Aug. 23, 2007

Related U.S. Application Data

(60) Provisional application No. 60/772,347, filed on Feb. 10, 2006.

(51) Int. Cl.
G01N 33/26 (2006.01)
G01N 33/00 (2006.01)

(52) U.S. Cl. .................... 436/60; 436/61; 436/119; 436/73; 436/79; 73/53.05; 73/53.01

(58) Field of Classification Search .................. 252/39; 250/339; 436/60, 61; 508/485, 486, 392; 73/54.04

See application file for complete search history.

(56) References Cited

U.S. PATENT DOCUMENTS

| | | | |
|---|---|---|---|
| 4,865,754 A * | 9/1989 | Chang | 508/392 |
| 5,537,336 A | 7/1996 | Joyce | |
| 5,558,802 A | 9/1996 | Dowling | |
| 5,800,782 A | 9/1998 | Hagstrom et al. | |
| 5,982,847 A | 11/1999 | Nelson | |
| 5,987,976 A | 11/1999 | Sarangapani | |
| 6,561,010 B2 * | 5/2003 | Wilson et al. | 73/54.04 |
| 6,779,505 B2 | 8/2004 | Reischman et al. | |
| 2001/0013247 A1 * | 8/2001 | Wilson et al. | 73/54.01 |
| 2003/0101801 A1 | 6/2003 | Wilson et al. | |
| 2003/0164451 A1 * | 9/2003 | Reischman et al. | 250/339.12 |
| 2003/0194811 A1 | 10/2003 | Reischman et al. | |
| 2004/0123644 A1 | 7/2004 | Jakoby et al. | |

FOREIGN PATENT DOCUMENTS

| | | |
|---|---|---|
| BR | 9802773 A | 7/1998 |
| KR | 2003080671 A | 10/2003 |
| RU | 1786433 A1 | 1/1993 |
| WO | WO01/36966 A2 | 11/2000 |

OTHER PUBLICATIONS

Joanna A. Wolska, et al., "A Powerful Oil Analysis Tool," *Practicing Oil Analysis*, May/Jun. 2004, pp. 20-23.
J. Christopher, et al., "Determination of sulphur in trace levels in petroleum products by wavelength-dispersive X-ray fluorescence spectroscopy", *Fuel*, 80 (2001), pp. 1975-1979.
"Asoma Perfects Two Applications for Energy Dispersive X-Ray Fluorescence Analyzer", *Fuel Technology & Management*, V8, N. 7, Sep.-Oct. 1998), pp. 60-61.
Wang Ziping, et al., "Sulfur Analysis and Monitoring of Oil and Gas in Petrochemical Enterprises", *Petroleum Refinery Engineering*, 29/8, (Aug. 1999), pp. 68-72.
Mariko Kato, et al., "Evaluation of Useful Lifetime of Gas Engine Lubrication Oils—Suggestion of New Methods for Oil Analysis and Evaluation of Degradation of Full-synthetic Long Life Lubrication Oils", *Journal of the Japan Petroleum Institute*, 45, (1), (2002), pp. 1-9.
J. George Wills, "Lubrication Fundamentals", Mobil Oil Reference Books, 1980, Publisher: Marcel Dekker, Inc., New York, pp. 34-45.
"Guidelines for the Lubrication of Medium Speed Diesel Engines", *CIMAC*, No. 13, 1994.
"Guidelines for the Lubrication of Two-Stroke Crosshead Diesel Engines", *CIMAC*, No. 15, 1997.

* cited by examiner

*Primary Examiner*—Walter D Griffin
*Assistant Examiner*—Christine T Mui
(74) *Attorney, Agent, or Firm*—Gary P Katz

(57) ABSTRACT

The present invention provides a method for determining the TBN of a used lubricating oil by measuring with a single device at least one element, such as sulfur, and correlating the measured amount to the oil's TBN. Preferably, a spectroscopic device is used to make the measurement.

18 Claims, 4 Drawing Sheets

DETERMINATION OF TOTAL BASE NUMBER IN MARINE ENGINE LUBRICANTS BY ELEMENTS

This application claims benefit of Provisional Application 60/772,347 filed Feb. 10, 2006.

FIELD OF THE INVENTION

This invention is broadly concerned with monitoring the condition of used lubricants. More specifically, the present invention relates to an analytical method for determining total base number (TBN) of a lubricant based on the measurement of at least one key element in the oil.

BACKGROUND OF THE INVENTION

Chemical and physical analysis of lubricants is often used to provide information about the condition of the lubricant as well as the wear status of equipment in which the lubricant is used. Most often a lubricant sample is taken from the equipment in which it is used and is sent to the laboratory for analysis, where several analytical tests are performed to determine a number of chemical properties. Among the key analyses performed on engine oils are those for TBN and wear debris elements. Sending lubricant samples to a laboratory for analysis, however, does not provide the equipment operator any immediate information about the condition of the lubricant. This lapse in time can be critical to the operation of the equipment.

To help minimize the time required to obtained analytical results, various on-site or on-line devices have been proposed to monitor the condition of the lubricant as well as the wear status of the equipment being lubricated. Many of these devices include multiple analyzers. In this regard see, for example, U.S. Pat. No. 5,982,847; U.S. Pat. No. 6,561,010 B2; U.S. Pat. No. 5,987,976; US 2004/0123644 A1; U.S. Pat. No. 5,537,336; U.S. Pat. No. 6,779,505 B2; and PCT WO 01/36966 A2.

In U.S. Pat. No. 5,537,336 there is disclosed an oil test assembly that includes an infrared spectrometer (IR) and an emission spectrometer for measuring wear debris elements. TBN is one of the lube oil properties measured by IR.

Similarly, U.S. Pat. No. 6,561,010 B2 and PCT WO 01/36966 A2 disclose an apparatus for analyzing a machine fluid that also employs multiple sensors. In this instance at least one of the sensors is a viscosity sensor. Wear debris elements are measured by x-ray fluorescence (XRF) spectroscopy. TBN may be inferred by IR.

U.S. Pat. No. 6,779,505 B2 uses a similar method for controlling lube oil feed rates in certain diesel engine applications, where wear debris is measured by XRF and TBN is measured by IR.

U.S. Pat. No. 5,982,847 discloses a method for measuring wear metal in lubrication oils by XRF. Measurement of TBN is not taught.

US 2004/0123644 A1 discloses a method for measuring volatile components in an oil.

None of these devices measures TBN and wear debris elements with a single analyzer. Such a device is highly desired for many applications, since it decreases complexity and maintenance, resulting in increased reliability. A single on-line device would be highly advantageous for real-time analysis.

SUMMARY OF THE INVENTION

Broadly stated the present invention comprises determining a used lubricating oil's TBN by measuring with a single device the amount of at least sulfur in the lubricating oil and correlating the measured amount to its TBN.

In one embodiment of the invention a spectroscopic method is used to measure the amount of sulfur in a used lubricating oil, and the amount measured is correlated to its TBN.

In another embodiment of the invention a spectroscopic method is used to measure both the amount of sulfur, and at least one other element in a used oil, where the other element is selected from one which was present in the oil when unused (new oil).

In another embodiment of the invention, preferably x-ray fluorescence spectroscopy (XRF) is used to measure both the amount of sulfur, at least one other element in a used oil, where the other element is selected from one which was present in the oil when new, and at least one wear debris element, such as iron.

DETAILED DESCRIPTION OF THE INVENTION

By way of overview, the present invention simplifies the determination of the TBN of a used lubricating oil when the amount of at least sulfur in the oil is being analyzed. Heretofore, TBN, sulfur and other elements had to be measured by separate analyzers or sensors. This invention simplifies the measurement to a single analyzer or sensor. Indeed, the present invention is suitable for use in the laboratory and importantly in the field and is readily adaptable for use on-line.

Specifically, the present invention comprises measuring the amount of at least sulfur in a used lubricating oil, preferably spectroscopically, for example by XRF, and correlating the amount measured with the oil's TBN. This method is particularly useful when the sulfur content and the TBN content of the oil are known prior to use. The additional sulfur in the sample after use is directly related to the amount of sulfate formed due to the neutralization of sulfuric acid by the lube oil additives. Sulfuric acid is formed during the combustion of sulfur containing fuel. Sulfate formation and TBN depletion in the used oil are directly correlated.

Most engine lube oils, however, have been altered somewhat while in use. Some of the lighter fractions of the lube oil may be burned away, thus concentrating additives and contaminants. This complicates the calculation of increased sulfur due to sulfate formation. Thus, in one embodiment of the invention, an additional element present in the fresh (new) lubricant is also measured and used as an internal reference. Among such elements mention is made of calcium and magnesium. For example, marine engine lubricating oils are generally highly overbased; i.e., they contain relatively high amounts of calcium carbonate, and the measurement of calcium is, therefore, useful as an internal reference. Other lubricating oils may contain magnesium which could serve as an internal reference.

Among the spectroscopic methods for measuring sulfur and other elements, specific mention is made of inductively coupled plasma atomic emission spectroscopy (ICP-AES), rotating disk electrode atomic emission spectroscopy (RDE-AES) and x-ray fluorescence spectroscopy (XRF). XRF is preferred due to its robustness, portability and ability to analyze particulates larger than about ten microns.

The present invention is particularly suited for, but not limited to, the analysis of scrapedown cylinder oils from crosshead diesel engines, where in such oils the TBN depletion can be 70 mg KOH/g or greater, and these lubricants are all loss, i.e. the used oil is not circulated in a sump. Because XRF is capable of measuring sulfur accurately, the amount of sulfate formed in the scrapedown oil, due to the neutralization of sulfuric acid by the base, can be correlated to the TBN of the oil.

Figure 1:
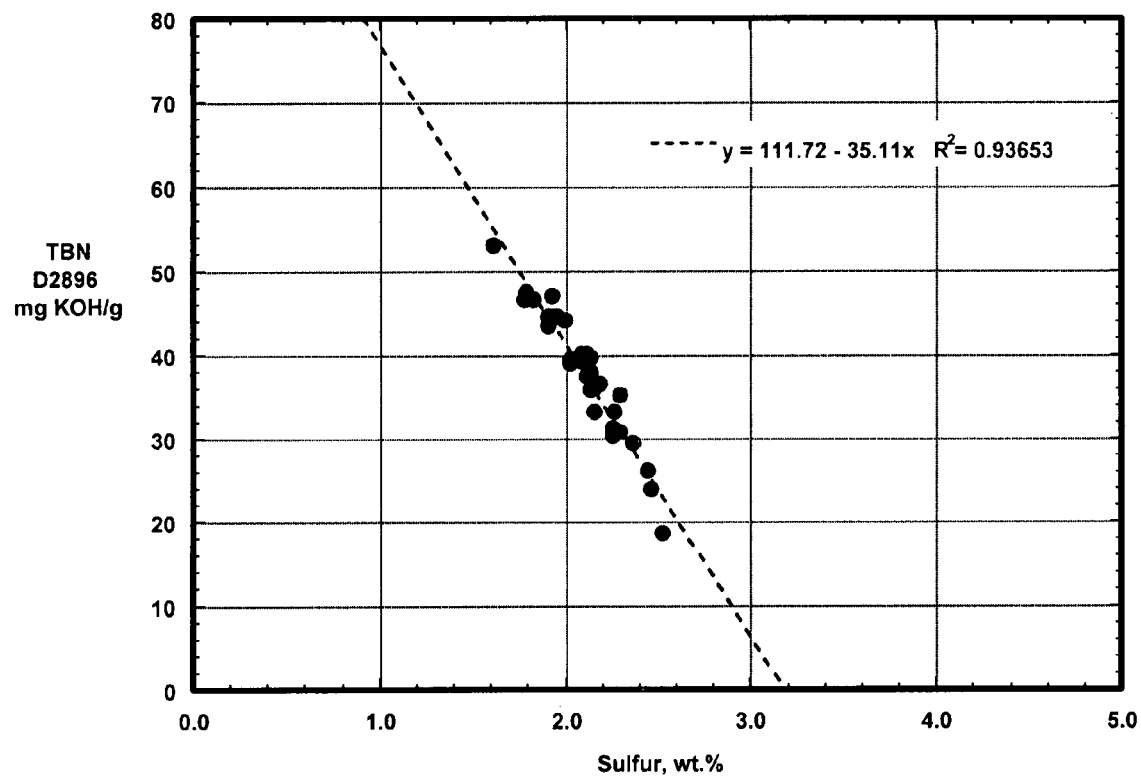
FIGS. 1 and 2 are plots of TBN versus sulfur for various scrapedown (used) cylinder oil samples.
Figure 3:
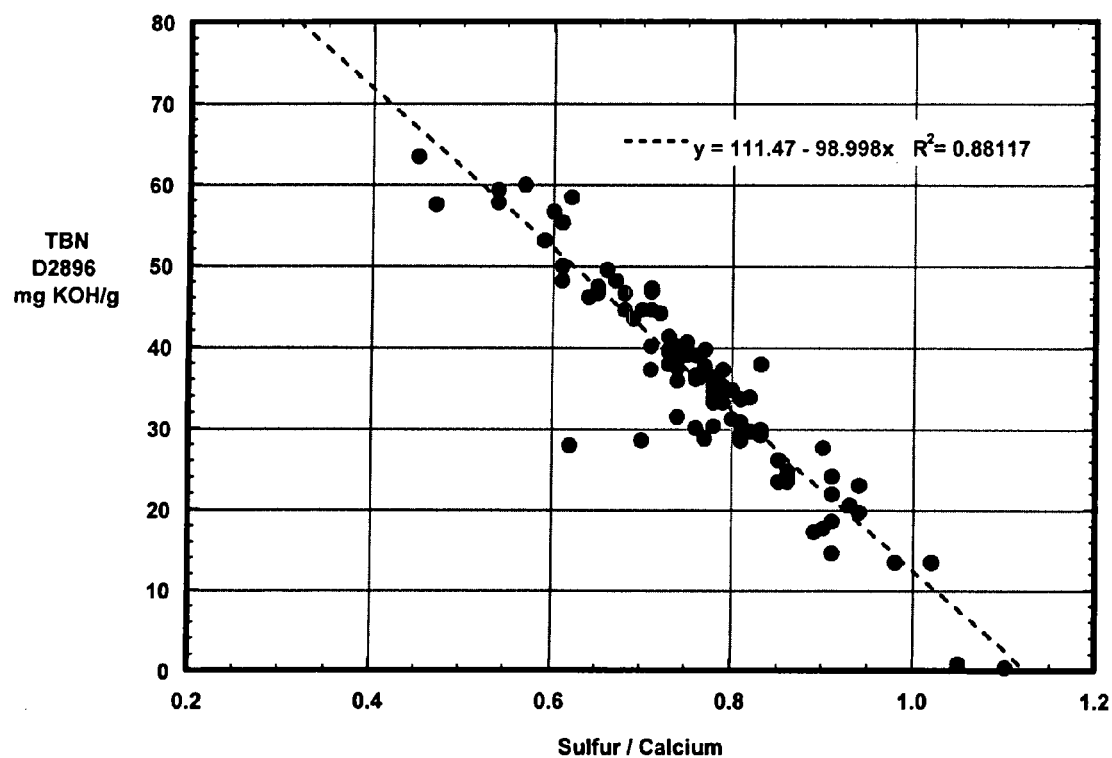
FIGS. 3 and 4 are plots of TBN versus the ratio of sulfur to calcium for various scrapedown cylinder oil samples.
Figure 4:
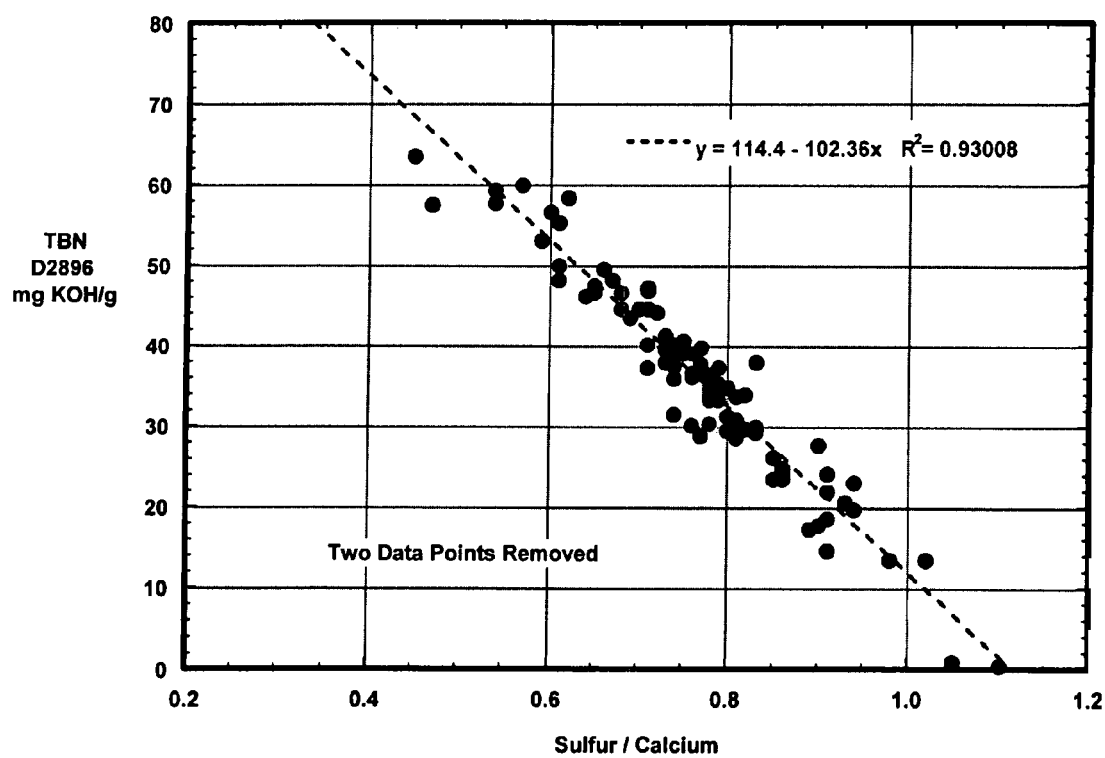

In the simplest cases, the measured sulfur is directly correlated to TBN as shown in FIG. 1. In this example all samples were collected from the same engine, and the correlation is very good. However, the good correlation is not maintained when samples from additional engines are included in the plot. See FIG. 2. A significantly improved correlation can be obtained if the sulfur results are normalized to a reference element, e.g. calcium. See FIG. 3. Normalization with a reference element is equally valid for the simplest cases. FIG. 4 shows the sample plot with just two data points removed.

Another important aspect of the present invention is that use of XRF spectroscopy to determine an oil's TBN also permits the measurement of wear elements in the oil such as iron, copper, chromium, lead, nickel, aluminum, tin and antimony using a single instrument.

EXAMPLES

The following non-limiting examples serve to demonstrate the invention.

Example 1

In this example 32 scrapedown (used) cylinder oil samples were collected from one marine vessel's crosshead diesel engine over a 4.5 month period. The TBN of the samples was measured by ASTM test method D2896, and the amount of sulfur in the oil was measured by XRF. A plot of TBN versus sulfur is shown in FIG. 1. As can be seen, there is a very good correlation between sulfur and TBN.

Example 2

Figure 2:
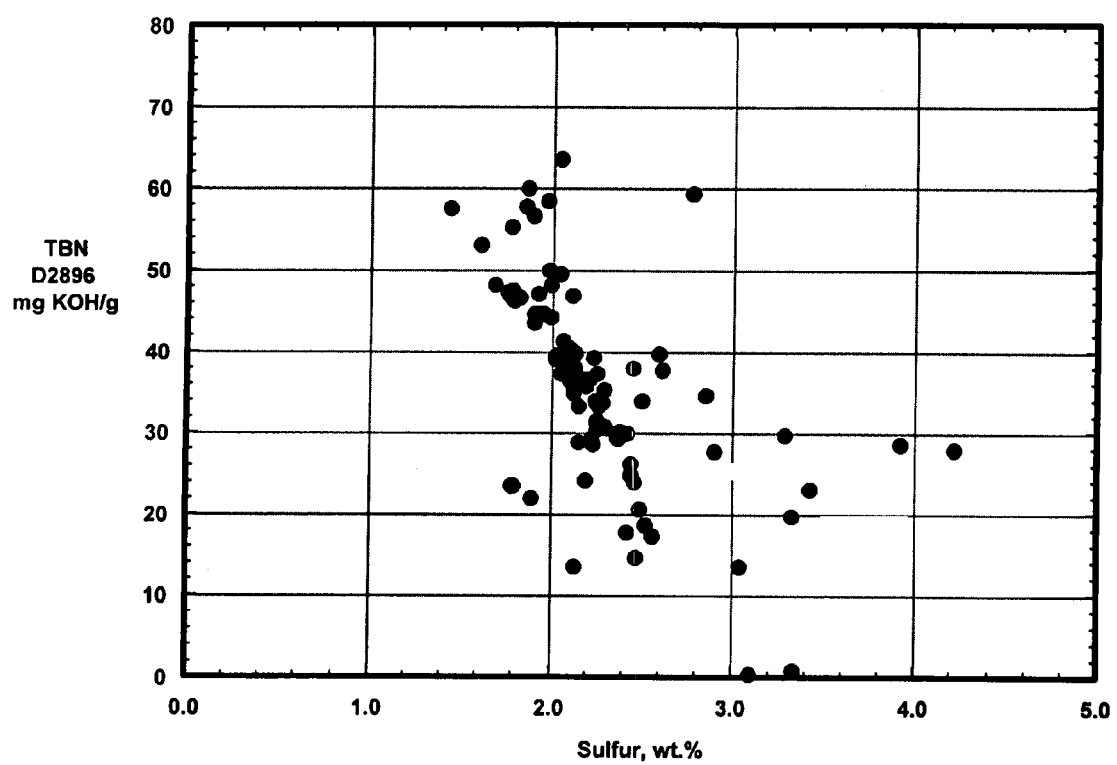

Scrapedown oil samples from 16 other vessels were analyzed in example 1. A plot of this data along with the data from example 1 is shown in FIG. 2. As can be seen, the correlation in this instance is poor apparently because each engine has its own combustion characteristics; however, when the amount of calcium was also determined, the sulfur to calcium ratio was found to correlate reasonably well with the oil's TBN as is shown in FIG. 3. FIG. 4 is a plot of the data of FIG. 3 with two data points that appear to be anomalous removed. Removal of these data points improves the correlation from $R^2=0.88$ to $R^2=0.93$.

What is claimed is:

1. A method comprising:
    a) monitoring TBN of used lubricating oil in equipment comprising:
        i. measuring with a single device the amount of at least sulfur in the used lubricating oil;
        ii. correlating the measured amount of at least sulfur directly to TBN;
        iii. determining the TBN by using the measured amount of at least sulfur in the correlation; and
    b) using the TBN to determine the condition of the used lubricating oil in the equipment.

2. The method of claim 1 wherein the amount of sulfur is measured spectroscopically.

3. The method of claim 2 including spectroscopically measuring the amount of at least one other element selected from one which was present in the oil when unused and using that measurement as an internal reference.

4. The method of claim 2 or 3 wherein the spectroscopic method is selected from the group consisting of ICP-AES, RDE-AES and XRF.

5. The method of claim 3 wherein the amount of sulfur and at least one other element in the lubricating oil is measured by XRF.

6. The method of claim 3 or 5 wherein one other element is calcium.

7. The method of claim 3 including measuring at least one wear element.

8. A method comprising:
    a) monitoring TBN of used marine lubricating oil in a marine engine comprising:
        i. spectroscopically measuring the amount of at least sulfur in the oil with a device;
        ii. correlating the measured amount of at least sulfur directly with TBN; and
        iii. determining the TBN by using the measured amount of at least sulfur in the correlation;
    b) using the TBN of used marine lubricating oil to determine the condition of the used marine lubricating oil in the marine engine.

9. The method of claim 8 including spectroscopically measuring the amount of at least one other element selected from those which were present in the oil when unused and using that measurement as an internal reference.

10. The method of claim 9 wherein the amount of sulfur and at least one other element is measured spectroscopically by a method selected from the group consisting of ICP-AES, RDE-AES and XRF.

11. The method of claim 9 wherein the one other element is calcium.

12. The method of claim 11 including spectroscopically measuring the amount of at least one wear element in the oil, thereby determining the oil's TBN and the amount of at least one wear element with a single instrument.

13. The method of claim 1 further comprising determining the wear status of the equipment from the measured at least one wear element.

14. The method of claim 7 further comprising determining the wear status of the equipment from the measured at least one wear element.

15. The method of claim 1 wherein the device is on the equipment.

16. The method of claim 8 wherein the device is on the marine engine.

17. The method of claim 1 wherein the sulfur is measured and TBN is determined with a single device.

18. The method of claim 8 wherein the sulfur is measured and TBN is determined with a single device.

* * * * *